(12) United States Patent
Peng et al.

(10) Patent No.: US 11,600,387 B2
(45) Date of Patent: Mar. 7, 2023

(54) CONTROL METHOD AND REINFORCEMENT LEARNING FOR MEDICAL SYSTEM

(71) Applicant: HTC Corporation, Taoyuan (TW)

(72) Inventors: Yu-Shao Peng, Taoyuan (TW); Kai-Fu Tang, Taoyuan (TW); Edward Chang, Taoyuan (TW); Hsuan-Tien Lin, Taoyuan (TW)

(73) Assignee: HTC Corporation, Taoyuan (TW)

( * ) Notice: Subject to any disclaimer, the term of this patent is extended or adjusted under 35 U.S.C. 154(b) by 962 days.

(21) Appl. No.: 16/414,794

(22) Filed: May 17, 2019

(65) Prior Publication Data

US 2019/0355471 A1 Nov. 21, 2019

Related U.S. Application Data

(60) Provisional application No. 62/772,637, filed on Nov. 29, 2018, provisional application No. 62/673,144, filed on May 18, 2018.

(51) Int. Cl.
*G16H 50/20* (2018.01)
*G16H 10/60* (2018.01)
*G06N 3/08* (2006.01)

(52) U.S. Cl.
CPC ............... *G16H 50/20* (2018.01); *G06N 3/08* (2013.01); *G16H 10/60* (2018.01)

(58) Field of Classification Search
CPC .......... G16H 50/20; G16H 10/60; G06N 3/02; G06Q 10/40; G06Q 10/00; G06Q 10/60

(Continued)

(56) References Cited

U.S. PATENT DOCUMENTS

2005/0209890 A1 9/2005 Kong
2012/0084092 A1 4/2012 Kozuch et al.
(Continued)

FOREIGN PATENT DOCUMENTS

CN 101263499 A 9/2008
CN 106709254 A 5/2017
(Continued)

OTHER PUBLICATIONS

UCL Press, "An introduction to neural networks", Taylor & Francis e-Library, 2004.
(Continued)

*Primary Examiner* — Edwyn Labaze
(74) *Attorney, Agent, or Firm* — CKC & Partners Co., LLC

(57) ABSTRACT

A control method for a reinforcement learning system includes following operations. The reinforcement learning system obtains training data relating to an interaction system. The interaction system interacts with a reinforcement learning agent. A neural network model is utilized by the reinforcement learning agent for selecting sequential actions from a set of candidate actions. The neural network model is trained to maximize cumulative rewards collected by the reinforcement learning agent in response to the sequential actions. During training of the neural network model, auxiliary rewards of the cumulative rewards are provided to the reinforcement learning agent according to a comparison between symptom inquiry actions of the sequential actions and diagnosed symptoms in the training data.

18 Claims, 13 Drawing Sheets

(58) Field of Classification Search
USPC ....... 706/21, 15, 16, 12, 13, 6; 235/375, 385
See application file for complete search history.

(56) References Cited

U.S. PATENT DOCUMENTS

| | | | |
|---|---|---|---|
| 2013/0268203 A1 | 10/2013 | Pyloth | |
| 2015/0370993 A1* | 12/2015 | Moturu | G16H 50/50 |
| | | | 703/6 |
| 2016/0196402 A1 | 7/2016 | Higashi | |
| 2018/0046773 A1* | 2/2018 | Tang | G16H 40/20 |
| 2019/0150867 A1* | 5/2019 | Itou | A61B 6/504 |
| 2019/0171438 A1* | 6/2019 | Franchitti | G06F 16/903 |
| 2019/0348178 A1* | 11/2019 | Eleftherou | G16H 10/60 |
| 2020/0341976 A1* | 10/2020 | Aggarwal | G06N 3/08 |
| 2021/0166816 A1* | 6/2021 | Khan | G06Q 10/1093 |

FOREIGN PATENT DOCUMENTS

| | | | |
|---|---|---|---|
| CN | 107451388 A | 12/2017 | |
| CN | 107545148 A | 1/2018 | |
| CN | 107729710 A | 2/2018 | |
| CN | 107910060 A | 4/2018 | |
| TW | 201805887 A | 2/2018 | |
| WO | 2018083671 A1 | 5/2018 | |
| WO | WO-2018083671 A1 * | 5/2018 | ............. G06N 20/00 |

OTHER PUBLICATIONS

Ya Zhang et al., "The Prediction Model of Disease Symptoms Based on BP Neural Network", Software Guide, vol. 16, No. 12, Dec. 2017.
Corresponding Chinese office action dated Oct. 11, 2021.
Corresponding Taiwan office action dated Jul. 7, 2020.
Corresponding Taiwan office action dated Apr. 7, 2021.

* cited by examiner

US 11,600,387 B2

CONTROL METHOD AND REINFORCEMENT LEARNING FOR MEDICAL SYSTEM

RELATED APPLICATIONS

This application claims priority to U.S. Provisional Application Ser. No. 62/673,144, filed May 18, 2018, and U.S. Provisional Application Ser. No. 62/772,637, filed Nov. 29, 2018, which are herein incorporated by reference.

BACKGROUND

Field of Invention

The disclosure relates to a machine learning method. More particularly, the disclosure relates to a reinforcement learning method for a medical system.

Description of Related Art

Recently the concept of computer-aided medical system has emerged in order to facilitate self-diagnosis for patients. The computer aided medical system may request patients to provide some information, and then the computer aided medical system may provide a diagnosis of the potential diseases based on the interactions with those patients.

SUMMARY

The disclosure provides a control method, which is suitable for a reinforcement learning system. An interaction system obtains training data related to the interaction system. The interaction system interacts with a reinforcement learning agent. The reinforcement learning agent is configured for selecting sequential actions. The training data includes a medical record indicating a relationship between a diagnosed disease and diagnosed symptoms related to the diagnosed disease. A neural network model is trained to maximize cumulative rewards collected by the reinforcement learning agent in response to the sequential actions. The neural network model is utilized by the reinforcement learning agent for selecting the sequential actions from a set of candidate actions. The sequential actions include symptom inquiry actions and a result prediction action. During training of the neural network model, auxiliary rewards of the cumulative rewards are provided to the reinforcement learning agent according to a comparison between the symptom inquiry actions and the diagnosed symptoms, and also a main reward of the cumulative rewards is provided to the reinforcement learning agent according to a comparison between the result prediction action and the diagnosed disease.

The disclosure provides a medical system, which includes an interaction system, a reinforcement learning agent and a neural network model. The reinforcement learning agent interacts with the interaction system. The reinforcement learning agent is configured to select sequential actions. The neural network model is trained by the reinforcement learning agent in reference to interactions between the interaction system and the reinforcement learning agent according to training data. The training data includes a medical record indicating a relationship between a diagnosed disease and diagnosed symptoms related to the diagnosed disease. The neural network model is utilized by the reinforcement learning agent for selecting the sequential actions from a set of candidate actions. The neural network model is trained to maximize cumulative rewards collected by the reinforcement learning agent in response to the sequential actions. The sequential actions include symptom inquiry actions and a result prediction action. During training of the neural network model, the interaction system provides auxiliary rewards of the cumulative rewards to the reinforcement learning agent according to a comparison between the symptom inquiry actions and the diagnosed symptoms, and the interaction system provides a main reward of the cumulative rewards to the reinforcement learning agent according to a comparison between the result prediction action and the diagnosed disease.

It is to be understood that both the foregoing general description and the following detailed description are demonstrated by examples, and are intended to provide further explanation of the invention as claimed.

BRIEF DESCRIPTION OF THE DRAWINGS

The disclosure can be more fully understood by reading the following detailed description of the embodiment, with reference made to the accompanying drawings as follows.

DETAILED DESCRIPTION

Figure 1:
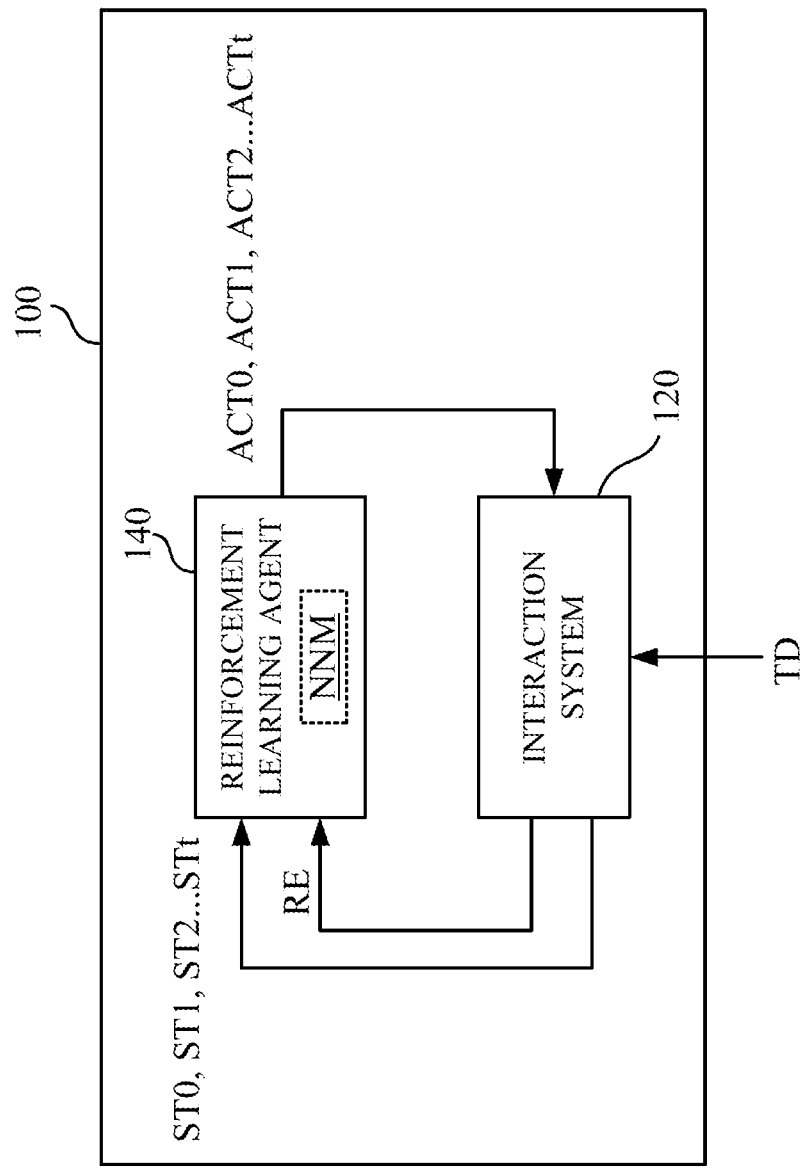
FIG. 1 is a schematic diagram illustrating a medical system in a training phase according to some embodiments of the disclosure.

Reference will now be made in detail to the present embodiments of the disclosure, examples of which are illustrated in the accompanying drawings. Wherever possible, the same reference numbers are used in the drawings and the description to refer to the same or like parts.

Reference is made to FIG. 1, which is a schematic diagram illustrating a medical system 100 in a training phase according to some embodiments of the disclosure. As shown in FIG. 1, the medical system 100 in the training phase includes an interaction system 120 and a reinforcement learning agent 140. The interaction system 120 and the reinforcement learning agent 140 interact with each other to train a neural network model NNM. The reinforcement learning agent 140 is configured to select sequential actions to cause the interaction system 120 to move from one state to another next state. The neural network model NNM is trained by the reinforcement learning agent 140 in reference to interactions between the interaction system 120 and the reinforcement learning agent 140 according to training data TD.

In some embodiments, the interaction system 120 and the reinforcement learning agent 140 can be implemented by a processor, a central processing unit or a computation unit. During a training phase of the medical system 100, the reinforcement learning agent 140 can be utilized to train the neural network model NNM (e.g., adjusting weights or parameters of nodes or interconnection links of the neural network model NNM) for selecting the sequential actions. During a training phase of the medical system 100, the interaction system 120 can be utilized as a supervisor of the training process on the reinforcement learning agent 140, such as the interaction system 120 will evaluate the sequential actions selected by the reinforcement learning agent 140 and provide corresponding rewards to the reinforcement learning agent 140. In some embodiments, the reinforcement learning agent 140 trains the neural network model NNM in order to maximize the rewards collected from the interaction system 120.

The neural network model NNM is utilized by the reinforcement learning agent 140 for selecting the sequential actions from a set of candidate actions. The sequential actions selected by the reinforcement learning agent 140 include some symptom inquiry actions and a result prediction action after the symptom inquiry actions.

In some embodiments, the result prediction action includes a disease prediction action. In some other embodiments, the result prediction action includes a medical department recommendation action corresponding to the disease prediction action. In still other embodiments, the result prediction action include both of the disease prediction action and the corresponding medical department recommendation action. In following demonstrational embodiments, the result prediction action selected by the reinforcement learning agent 140 includes the disease prediction action. However, the disclosure is not limited thereto.

When the reinforcement learning agent 140 selects proper actions (a proper symptom inquiry action or a correct disease prediction action), corresponding rewards will be provided by the interaction system 120 to the reinforcement learning agent 140. In some embodiments, the reinforcement learning agent 140 trains the neural network model NNM to maximize cumulative rewards collected by the reinforcement learning agent 140 in response to the sequential actions, such that the neural network model NNM will be trained to select proper symptom inquiries to ask and select the correct disease prediction at its best.

Figure 2A:
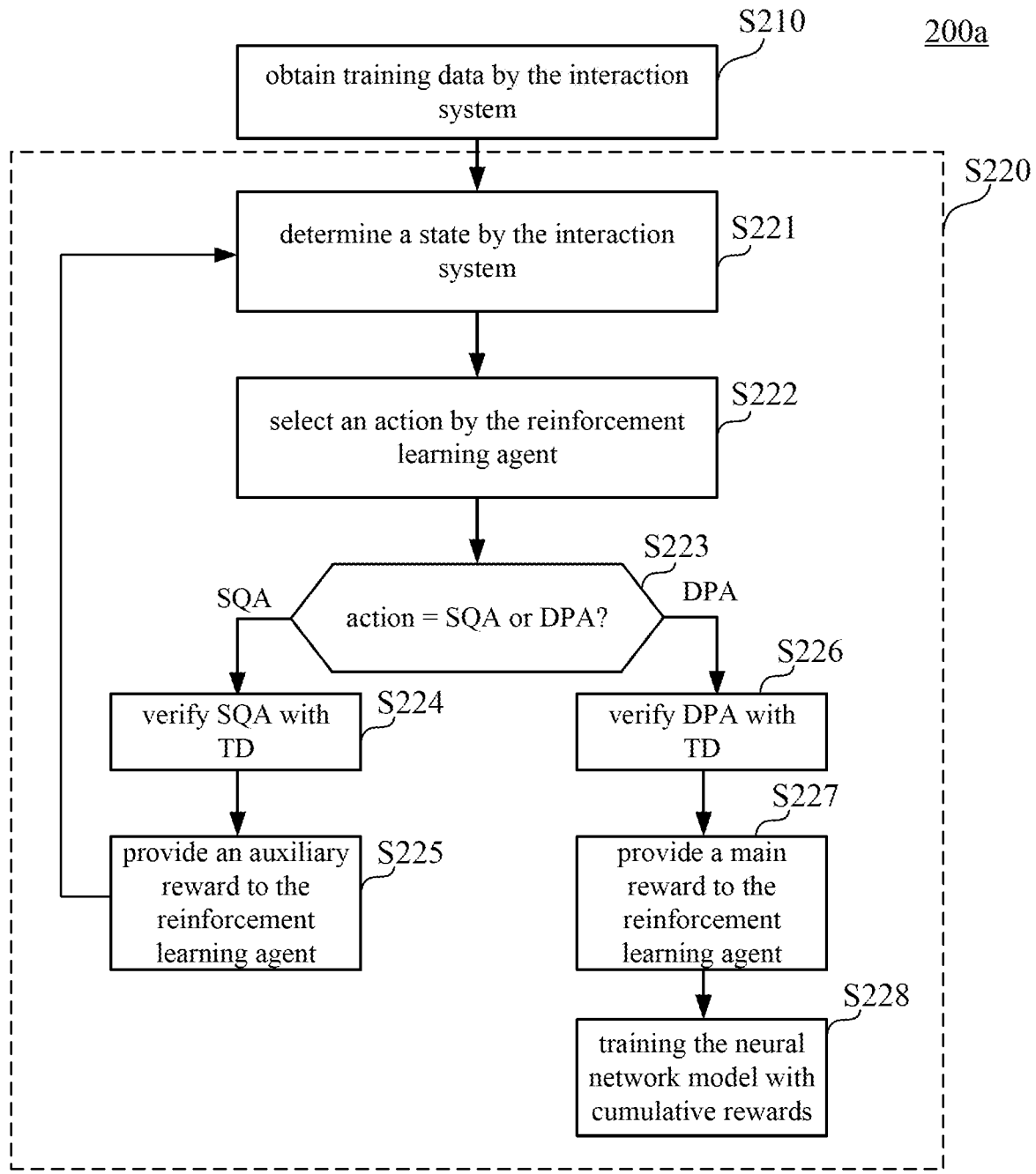
FIG. 2A is a flow chart illustrating a control method about how the neural network model is trained by the medical system in FIG. 1 according to some embodiments of the disclosure.

Reference is further made to FIG. 2A, which is a flow chart illustrating a control method 200a about how the neural network model NNM is trained by the medical system 100 in FIG. 1 according to some embodiments of the disclosure.

As shown in FIG. 1 and FIG. 2A, operation S210 of the control method 200a is performed by the interaction system 120 to obtain training data TD relating to the medical system 100. In some embodiments, the training data TD includes known medical records. The medical system 100 utilizes the known medical records in the training data TD to train the neural network model NNM. In an example, the training data TD can be obtained from data and statistics information from the Centers for Disease Control and Prevention (https://www.cdc.gov/datastatistics/index.html).

Figure 3:
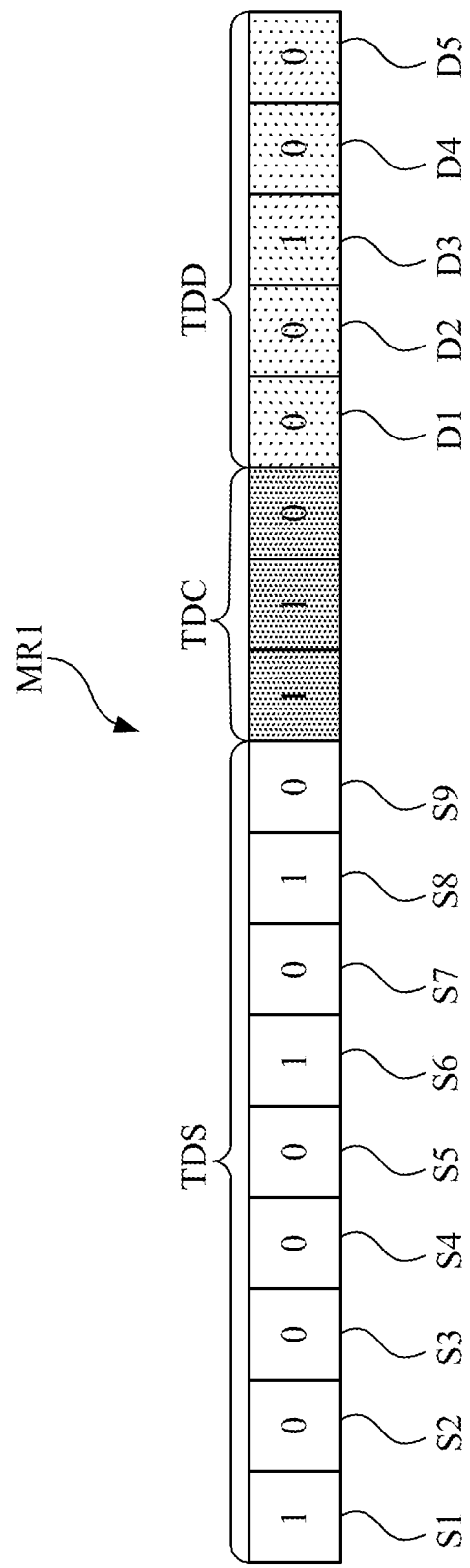
FIG. 3 is a schematic diagram illustrating one medical record in the training data according to some embodiments of the disclosure.

Reference is further made to FIG. 3, which is a schematic diagram illustrating one medical record MR1 in the training data TD according to some embodiments of the disclosure. In the embodiments shown in FIG. 3, the medical record MR1 in the training data TD includes diagnosed symptom information TDS, context information TDC and diagnosed disease information TDD. The data bits "1" in the diagnosed symptom information TDS means that a patient mentioned in the medical record MR1 suffers the specific diagnosed symptom. The data bits "0" in the diagnosed symptom information TDS means that the patient does not have the specific diagnosed symptom. As shown in FIG. 3, the diagnosed symptoms S1, S6 and S8 occurs to the patient, and the other symptoms S2-S5, S7 and S9 does not happen to the patient. The data bit "1" in the diagnosed disease information TDD means that the patient has the specific diagnosed disease. The data bits "0" in the diagnosed disease information TDD means that the patient does not have the specific diagnosed disease. As shown in FIG. 3, the patient mentioned in the medical record MR1 has the diagnosed disease D3.

As shown in FIG. 3, the medical record MR1 indicates a relationship between a diagnosed disease D3 and diagnosed symptoms S1, S6 and S8 related to the diagnosed disease D3. The medical record MR1 may record the diagnosed disease D3 of a patient and also corresponding symptoms (the diagnosed symptoms S1, S6 and S8) occurring to the patient when the patient suffers the diagnosed disease D3. Therefore, the medical record MR1 may imply an interrelationship between the possible diseases D1-D5 and the possible symptoms S1-S9. When a patient in another medical record (not shown) has another disease, the patient may have different symptoms corresponding to the disease. Even when two patients suffer the same disease, the two patients may have symptoms not exactly the same.

It is noticed that, the medical record MR1 having five possible diseases D1-D5 and nine possible symptoms S1-S9 is illustrated in FIG. 3 for demonstration. However, the disclosure is not limited thereto. In some embodiments, the medical records in the training data TD may have about 200 to 500 possible symptoms corresponding to about 200 to 500 possible diseases. The medical record MR1 merely illustrates a small part of the possible symptoms S1-S9 and the possible diseases D1-D5 for briefly demonstrating.

The medical record MR1 in FIG. 3 shows that the patient has the diagnosed disease D3 (not the disease D1, D2, D4 or D5) and the patient suffers the diagnosed symptoms S1, S6 and S8 (without the symptoms S2-S5, S7 and S9). When the patient has different diagnosed diseases and different diagnosed symptoms, the data bits in the medical record will be different.

In some embodiments as illustrated in FIG. 3, the medical record MR1 may further include context information TDC of the patient. The context information TDC may indicate a gender, an age, a blood pressure, a mental status, a marriage status, a DNA table, or any other related information about the patient. In some embodiments, the context information TDC in the medical record MR1 is also utilized in training the neural network model NNM.

As shown FIG. 1 and FIG. 2A, operation S220 of the control method 200a is performed by the interaction system 120 and the reinforcement learning agent 140, to train the neural network model NNM according to the medical record MR1 in the training data TD as shown in FIG. 3. It is noticed that FIG. 3 illustrate one medical record MR1 in the training data TD for training the neural network model NNM. In practical applications, the training data TD may include about 100 to about 1000000 medical records. The training process discussed in operation S220 will be repeated many times to optimize the trained neural network model NNM.

Figure 4A:
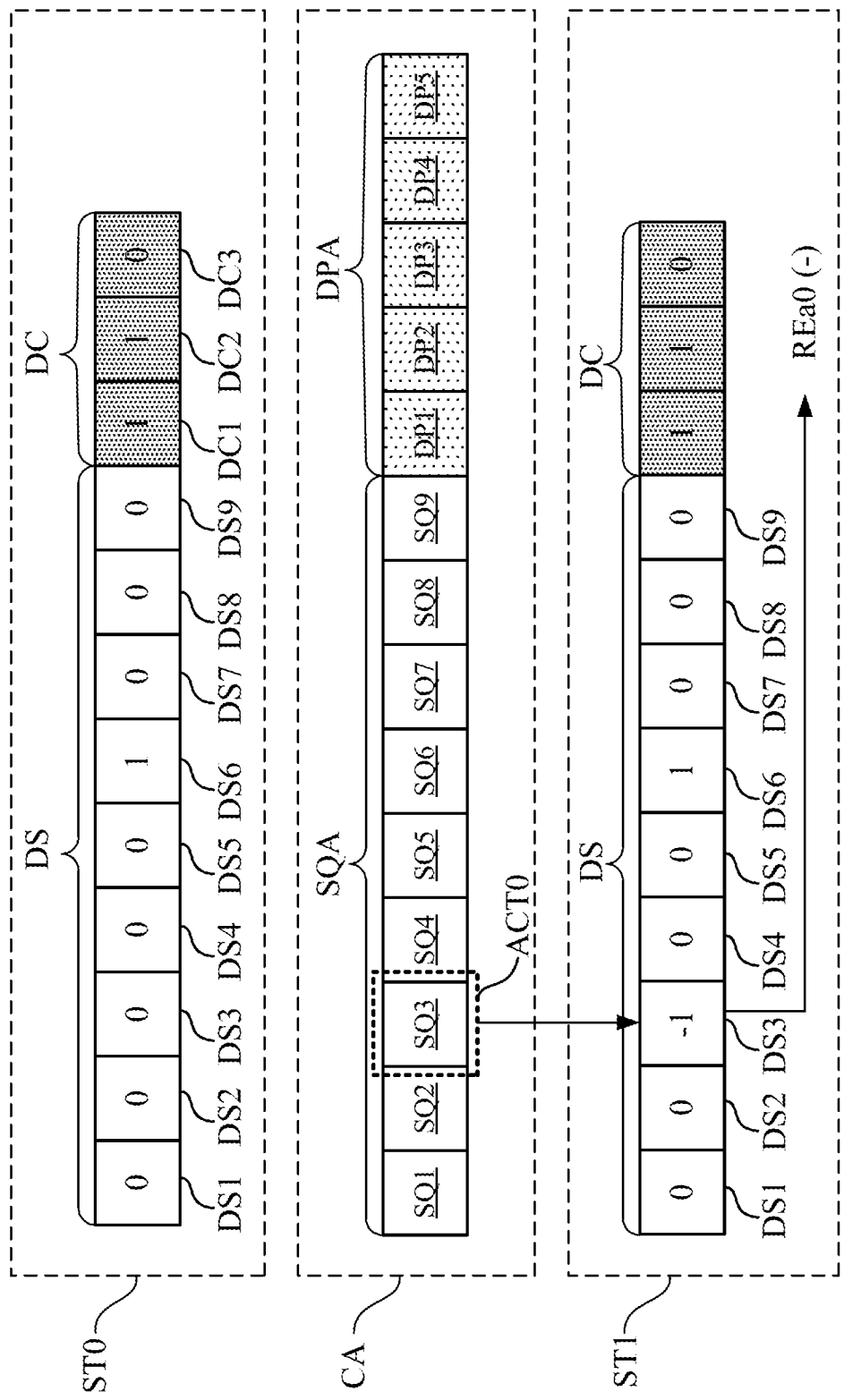
FIG. 4A is a schematic diagram illustrating states and an action determined by the control method in some embodiments.

As embodiments shown FIG. 2A, operation S220 of the control method 200a include operations S221-S228. As shown in FIG. 1 and FIG. 2A, at the beginning, the operation S221 is performed to determine a state by the interaction system 120 according to the medical record MR1 in the training data TD. Reference is further made to FIG. 4A, which is a schematic diagram illustrating states ST0-ST1 and an action ACT0 determined by the control method 200a in some embodiments.

In an example, the interaction system 120 determines the state ST0 as shown in embodiments of FIG. 4A. The state ST0 includes symptom data bits DS and context data bits DC. Each data bit DS1-DS9 of the symptom data bits DS can be configured to 1 (a positive status means the symptom occurs), −1 (a negative status means the symptom does not occur) or 0 (an unconfirmed status means it is not sure whether the symptom occurs or not). Each data bits DC1-DC3 of the context data bits DC indicate related information of the patient in the medical record. The data bits in the context data bits may indicate a gender, an age, a blood pressure, a mental status, a marriage status, a DNA table, or any other related information about the patient. For example, the data bit DC1 "1" can indicate the patient is a male, and the data bit DC3 "0" can indicate the patient is not married. In practical applications, the context data bits DC may include more data bits (not shown in figures) to record the age, the blood pressure, the mental status, the DNA table, or any other related information about the patient.

In embodiments as shown in FIG. 4A, the data bits DC1-DC3 of the context data bits DC can be duplicated from the context information TDC in the medical record MR1 as shown in FIG. 3.

In embodiments as shown in FIG. 4A, the data bit DS6 of the symptom data bits DS is set as "1" by the interaction system 120 according to the diagnosed symptom S6 in the medical record MR1 as shown in FIG. 3. In the initial state ST0, only the data bit DS6 is known, "1", and other data bits DS1-DS5 and DS7-DS9 of the symptom data bits DS are unconfirmed, "0".

As shown in FIG. 1 and FIG. 2A, at the beginning, the operation S222 is performed, by the reinforcement learning agent 140 with the neural network model NNM, to select an action from a set of candidate actions according to the state ST0 (which includes the data bit DS6 indicating the sixth symptom occurs).

As shown in FIG. 4A, the set of candidate actions CA include nice candidate actions SQ1-SQ9 of the symptom inquiry actions SQA and five candidate actions DP1-DP5 of the disease prediction action DPA. When the candidate action SQ1 is selected, a query about the first symptom (corresponding to the symptom S1 in FIG. 3) will be executed. When the candidate action SQ2 is selected, another query about the second symptom (corresponding to the symptom S2 in FIG. 3) will be executed. When the candidate action SQ3 is selected, another query about the third symptom (corresponding to the symptom S3 in FIG. 3) will be executed. Similarly, when different symptom inquiry actions SQA are selected, the query about the corresponding symptoms will be executed.

On the other hand, when the candidate action DP1 is selected, a disease prediction about the first disease (corresponding to the disease D1 in FIG. 3) will be executed. When the candidate action DP2 is selected, a disease prediction about the second disease (corresponding to the disease D2 in FIG. 3) will be executed. Similarly, when one of the disease prediction actions DPA is selected, the disease prediction about the corresponding disease will be executed.

In some embodiments as shown in FIG. 1 and FIG. 2A, a budget "t" can be applied to the medical system 100 to decide how many symptom inquiries (i.e., how many actions from the symptom inquiry actions SQA) will be made before making a disease prediction (i.e., an action from the disease prediction actions DPA). In the following embodiments, the budget "t" is set at "3" for demonstration. In other words, the reinforcement learning agent 140 will select one of the symptom inquiry actions SQA for three cycles before selecting one of the disease prediction actions DPA.

On the other hand, when the budget "t" is expired, the reinforcement learning agent 140 as shown in FIG. 1 and FIG. 2A will select one candidate action from the disease prediction actions DPA. In some embodiments, the neural network model NNM, utilized by the reinforcement learning agent 140 for selecting the sequential actions, to maximize cumulative rewards collected by the reinforcement learning agent 140 in response to the sequential actions. The disclosure is not limited to that the budget "t=3". The budget "t" can be set at a positive integers larger than 1. In some embodiments, the budget "t" can be set about 5 to 9.

In some other embodiments, the budget "t" can be regarded as a maximum amount of symptom inquiries (i.e., how many actions from the symptom inquiry actions SQA) will be made before making the disease prediction (i.e., an action from the disease prediction actions DPA). However, the reinforcement learning agent 140 are not required to ask "t" symptom inquiries in every cases (e.g., patients or medical records in the training data TD). If the reinforcement learning agent 140 already gathers enough information to select one of the disease prediction actions DPA, the reinforcement learning agent 140 may select an action from the disease prediction actions DPA before the budget "t" is expired.

In some cases, the reinforcement learning agent 140 will receive a positive reward when the selected one of the disease prediction actions DPA is correct (matched with the diagnosed disease in the medical record of the training data TD). On the other hand, the reinforcement learning agent 140 will receive a negative reward when the selected one of the disease prediction actions DPA is wrong (not matched with the diagnosed disease in the medical record of the training data TD). In aforesaid cases, the reinforcement learning agent 140 will not directly receive the reward while selecting the symptom inquiry actions SQA. It is observed that, based on the medical records in the training data TD, one patient suffering a diagnosed disease usually has three to four corresponding diagnosed symptoms. According to some statistics of the medical records, one patient will suffer 3.07 to 3.19 symptoms. It is noticed that, in practical applications, there are many candidate actions (e.g., 300 or more) in the symptom inquiry actions SQA, the reinforcement learning agent 140 only select a limited number of symptom inquiry actions to ask before making the disease prediction. In aforesaid cases, most of the symptom inquiry actions will get an answer of "NO", and only a small part of the symptom inquiry actions will get an answer of "YES". Therefore, it is encouraged to select one of the symptom inquiry actions SQA having a potential answer of "YES", because it may provide more information (or even key information) to predict the disease. When the reward collected by the reinforcement learning agent 140 depends simply on the correctness of the disease prediction actions DPA, the training process does not directly encourage the reinforcement learning agent 140 to select the symptom inquiry actions with a potential answer of "YES".

Therefore, some embodiments of the medical system 100 will provide auxiliary rewards (other than the main reward related to the disease prediction actions DPA) corresponding to the symptom inquiry actions SQA.

As shown in embodiments of FIG. 4A, in operation S222, the candidate action SQ3 of the symptom inquiry actions SQA is selected by the reinforcement learning agent 140 to be the action ACT0. In operation S223, the current action is determined to be one of the symptom inquiry actions SQA. In response, operation S224 is performed, by the interaction system 120 or the reinforcement learning agent 140, to verify the selected candidate action SQ3 of the symptom inquiry actions SQA. The selected candidate action SQ3 is compared with the diagnosed symptoms in the medical record MR1 of the training data TD.

Based on the medical record MR1 of the training data TD shown in FIG. 3, an answer to the candidate action SQ3 of the symptom inquiry actions SQA is "NO". In response to the one of the symptom inquiry actions SQA failing to match the diagnosed symptoms in the training data TD, operation S225 is performed, to provide a negative auxiliary reward REa0(−) to the reinforcement learning agent 140 as shown in FIG. 4A. Because the budget is not expired yet, the control method 200a returns to operation S221 to determine an updated state ST1 by the interaction system 120. As shown in FIG. 4A, in the state ST1, the data bit DS3 of the symptom data bits DS is changed from unconfirmed "0" into negative "−1", which means that the third symptom does not happen. The control method 200a will continue the operation S222 in reference with the new state ST1.

Figure 4B:
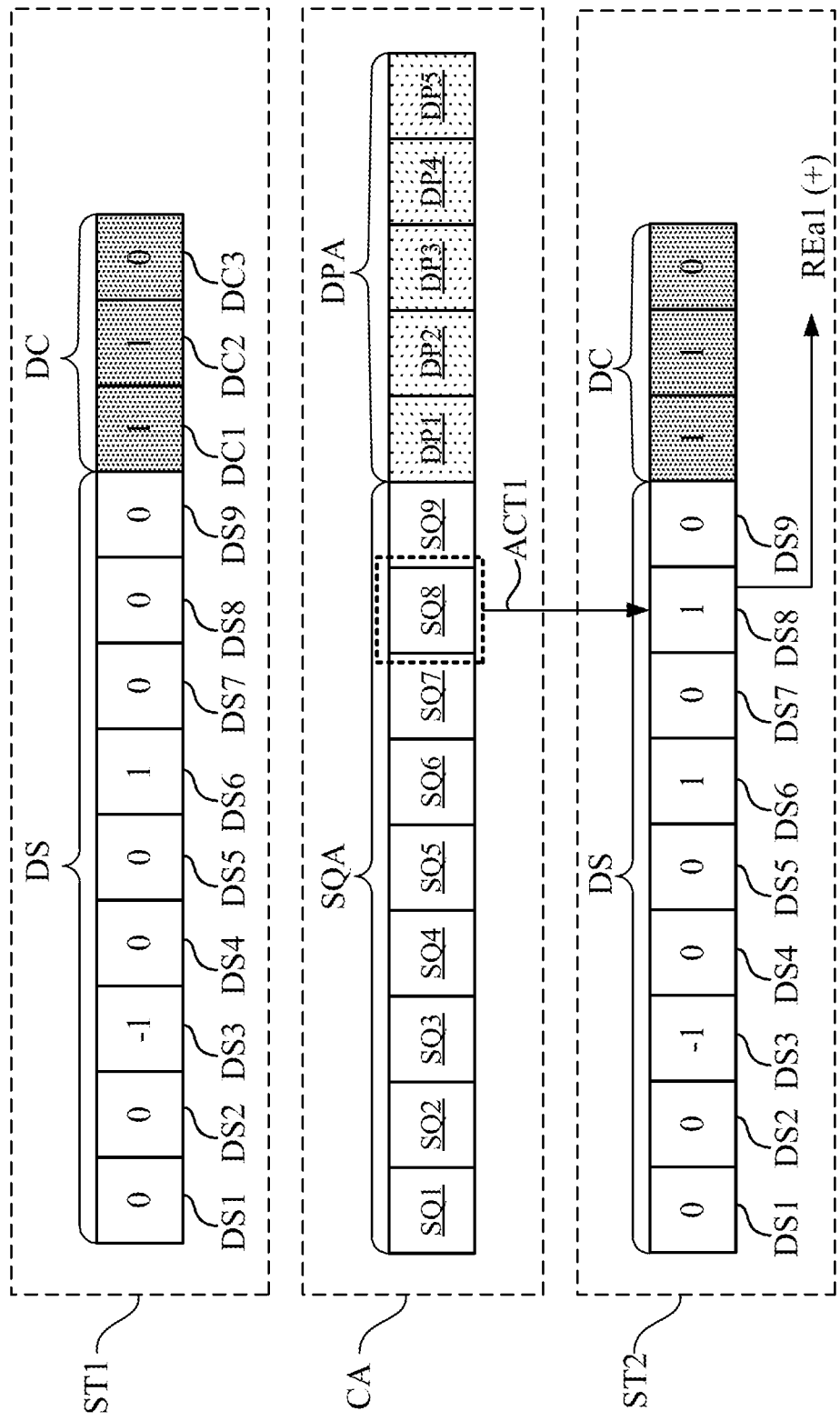
FIG. 4B is a schematic diagram illustrating states and another action determined by the control method in some embodiments.

Reference is further made to FIG. 4B, which is a schematic diagram illustrating states ST1-ST2 and another action ACT1 determined by the control method 200a in some embodiments.

As shown in FIG. 1, FIG. 2A and FIG. 4B, the operation S222 is performed, by the reinforcement learning agent 140 with the neural network model NNM, to select another action from a set of candidate actions according to the state ST1 (which includes the data bit DS6 indicating the sixth symptom occurs and the data bit DS3 indicating the third symptom does not occur).

As shown in embodiments of FIG. 4B, in operation S222, the candidate action SQ8 of the symptom inquiry actions SQA is selected by the reinforcement learning agent 140 to be the action ACT1. In operation S223, the current action is determined to be one of the symptom inquiry actions SQA. In response, operation S224 is performed, by the interaction system 120 or the reinforcement learning agent 140, to verify the selected candidate action SQ8 of the symptom inquiry actions SQA. The selected candidate action SQ8 is compared with the diagnosed symptoms in the medical record MR1 of the training data TD.

Based on the medical record MR1 of the training data TD shown in FIG. 3, an answer to the candidate action SQ8 of the symptom inquiry actions SQA is "YES". In response to the one of the symptom inquiry actions matching one of the diagnosed symptoms in the training data TD, operation S225 is performed, to provide a positive auxiliary reward REa1(+) to the reinforcement learning agent 140 as shown in FIG. 4B. Because the budget is not expired yet, the control method 200a returns to operation S221 to determine an updated state ST2 by the interaction system 120. As shown in FIG. 4B, in the state ST2, the data bit DS8 of the symptom data bits DS is changed from unconfirmed "0" into positive "1", which means that the eighth symptom happen. The control method 200a will continue the operation S222 in reference with the new state ST2.

Figure 4C:
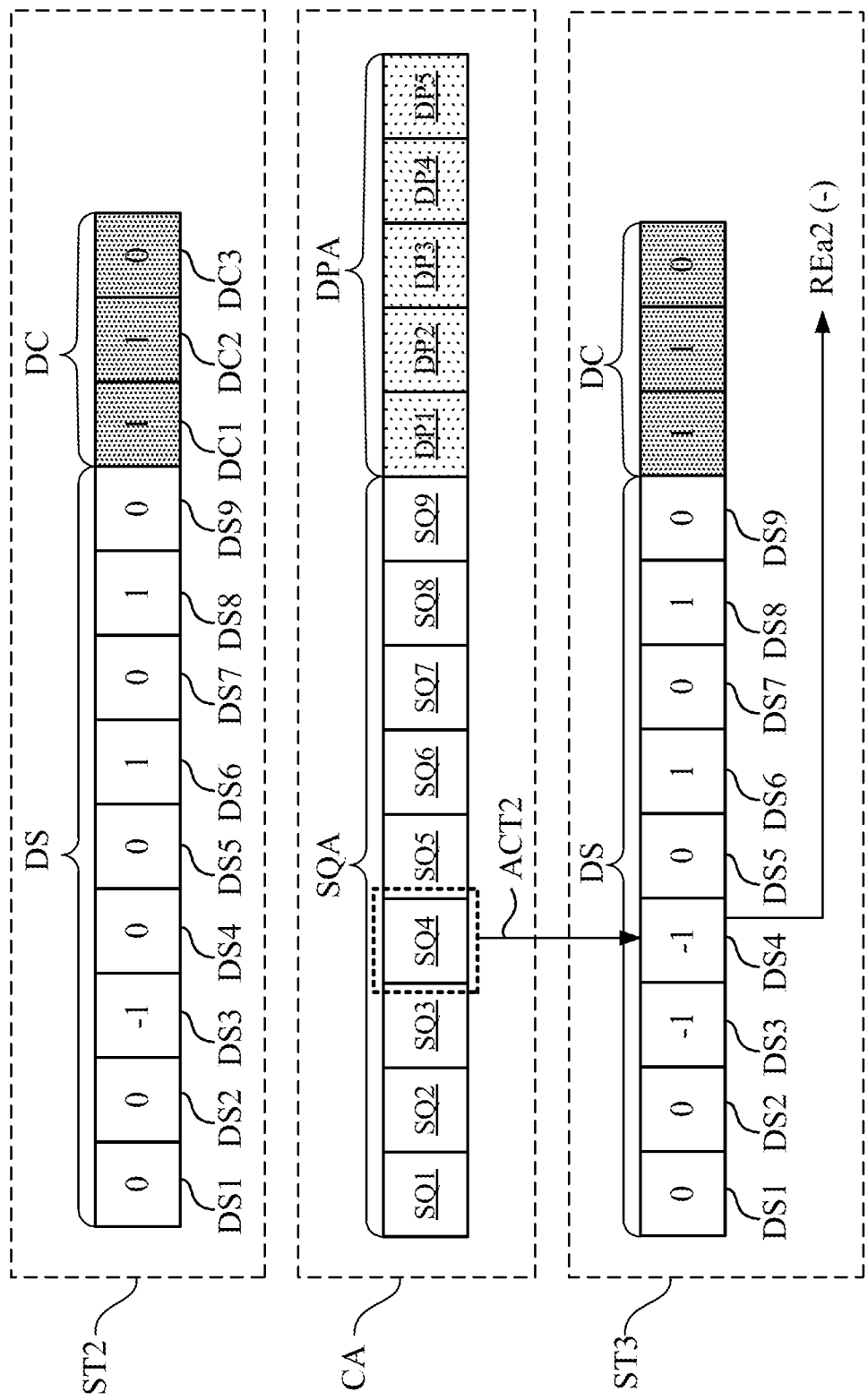
FIG. 4C is a schematic diagram illustrating states and another action determined by the control method in some embodiments.

Reference is further made to FIG. 4C, which is a schematic diagram illustrating states ST2-ST3 and another action ACT2 determined by the control method 200a in some embodiments.

As shown in FIG. 1, FIG. 2A and FIG. 4C, the operation S222 is performed, by the reinforcement learning agent 140 with the neural network model NNM, to select another action from a set of candidate actions according to the state ST2.

As shown in embodiments of FIG. 4C, in operation S222, the candidate action SQ4 of the symptom inquiry actions SQA is selected by the reinforcement learning agent 140 to be the action ACT2. In operation S223, the current action is determined to be one of the symptom inquiry actions SQA. In response, operation S224 is performed, by the interaction system 120 or the reinforcement learning agent 140, to verify the selected candidate action SQ4 of the symptom inquiry actions SQA. The selected candidate action SQ4 is compared with the diagnosed symptoms in the medical record MR1 of the training data TD.

In aforesaid embodiments, the current action at each stage is selected from unconfirmed ones of the symptom inquiry actions SQA. The reinforcement learning agent 140 shall avoid repeating the same symptom inquiry action, because it will waste time and provide no effective information. The interaction system 120 will verify whether the reinforcement learning agent 140 repeatedly select the same symptom inquiry action. In some embodiments, the interaction system 120 will compare a currently-selected action of the symptom inquiry actions and all of previously-selected actions of the symptom inquiry actions. If the currently-selected action and one of the previously-selected actions direct to the same symptom, the interaction system 120 will provide the negative auxiliary reward to the reinforcement learning agent 140.

Based on the medical record MR1 of the training data TD shown in FIG. 3, an answer to the candidate action SQ4 of the symptom inquiry actions SQA is "NO". In response to the one of the symptom inquiry actions SQA failing to match the diagnosed symptoms in the training data TD, operation S225 is performed, to provide another negative auxiliary reward REa2(−) to the reinforcement learning agent 140 as shown in FIG. 4C. The control method 200a returns to operation S221 to determine an updated state ST3 by the interaction system 120. As shown in FIG. 4C, in the state ST3, the data bit DS4 of the symptom data bits DS is changed from unconfirmed "0" into negative "−1", which means that the fourth symptom does not happen. The control method 200a will continue the operation S222 in reference with the new state ST3. In this round, the budget "t=3" is reached in this demonstrational example.

Figure 4D:
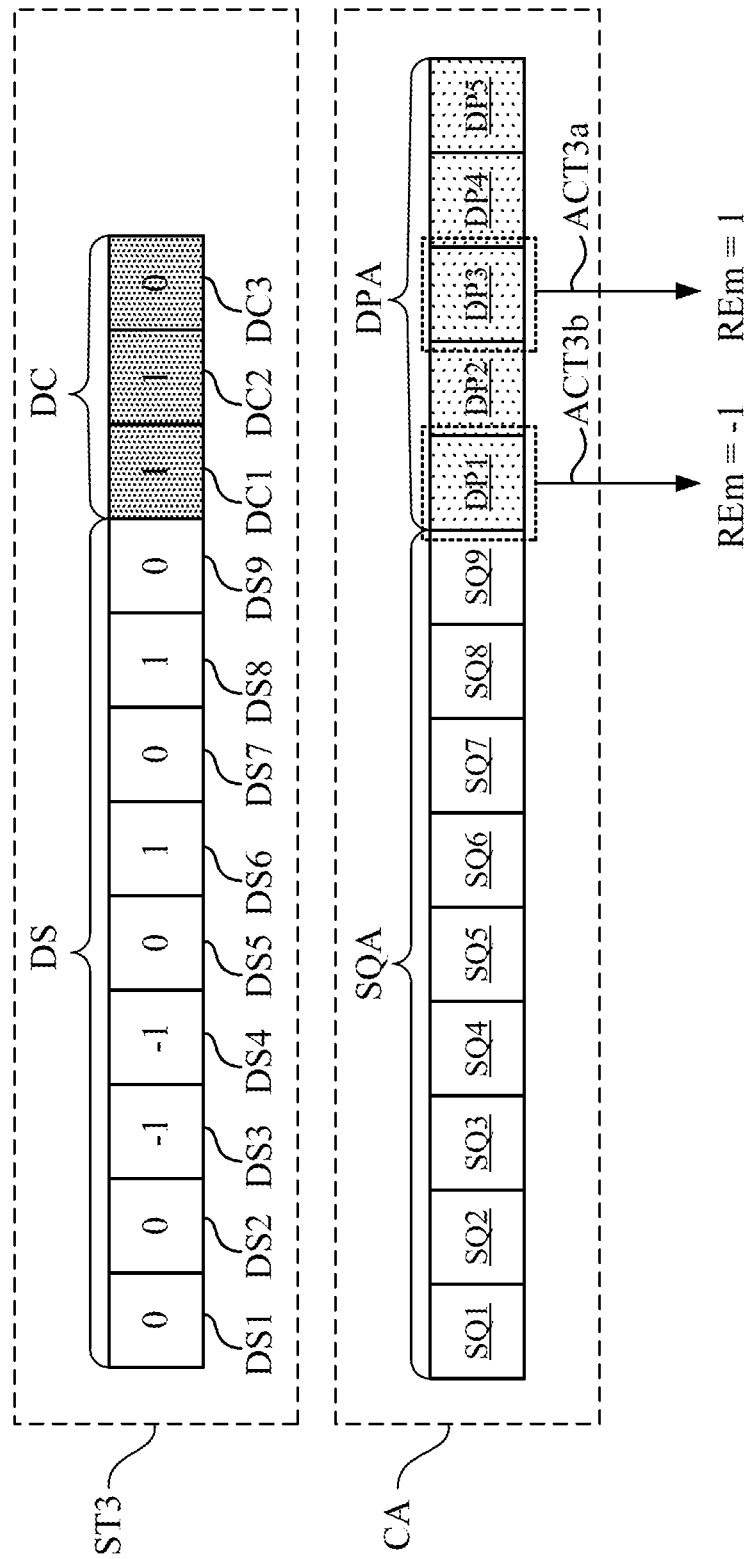
FIG. 4D is a schematic diagram illustrating a state and another action determined by the control method in some embodiments.

Reference is further made to FIG. 4D, which is a schematic diagram illustrating states ST3 and another action ACT3 determined by the control method 200a in some embodiments.

As shown in FIG. 1, FIG. 2A and FIG. 4D, the operation S222 is performed, by the reinforcement learning agent 140 with the neural network model NNM, to select another action from the five candidate actions DP1-DP5 of the disease prediction action DPA according to the state ST3.

It is assumed that if the candidate action DP3 of the disease prediction action DPA is selected, as the action ACT3a shown in FIG. 4D, a positive main reward REm "1" will be provided to the reinforcement learning agent 140. In this case, the cumulative rewards collected by the reinforcement learning agent will be:

$$REa0(-)+REa1(+)+REa2(-)+1$$

In another case, it is assumed that if the candidate action DP1 of the disease prediction action DPA is selected as the action ACT3b shown in FIG. 4D, there will be a negative main reward REm, REm=−1, provided to the reinforcement learning agent 140. In this case, the cumulative rewards collected by the reinforcement learning agent will be:

$$REa0(-)+REa1(+)+REa2(-)+(-1)$$

It is notice that, the neural network model NNM is trained to maximize the cumulative rewards collected by the reinforcement learning agent 140. Therefore, the neural network model NNM is trained to make the correct disease prediction to get the positive main reward "1". In the meantime, the neural network model NNM is also trained to ask proper symptom inquiry (in order to predict the correct disease prediction to obtain the positive auxiliary rewards). Even the auxiliary rewards addition to the original reward (the main reward) are provided by the control method 200a, the control method 200a can make sure the auxiliary rewards do not affect the original Markov decision process (MDP) by giving a proper boundary of the auxiliary rewards.

In some other embodiments, rewards corresponding to the sequential actions ACT0, ACT1, ACT2 and ACT3a/ACT3b in the sequential order are provided with gradually increasing discounts.

It is assumed that if the candidate action DP3 of the disease prediction action DPA is selected, as the action ACT3a shown in FIG. 4D, a positive main reward REm "1" will be provided to the reinforcement learning agent 140. In this case, the cumulative rewards collected by the reinforcement learning agent will be:

$$REa0(-)+[d*REa1(+)]+[d^2*REa2(-)]+[d^3*1]$$

In aforesaid equation, d is a discount factor to the rewards, and d is a positive value between 0 and 1. For example, d can be 0.99, 0.9, 0.8 or any suitable value.

In this case, the auxiliary reward REa0(−) corresponding to the action ACT0 is provided at an earlier state than another auxiliary reward [d*REa1(+)] corresponding to the action ACT1. In this case, the auxiliary reward REa0(−) is not provided with the discount factor, and the auxiliary reward [d*REa1(+)] is provided with the discount factor "d".

In this case, the auxiliary reward [d*REa1(+)] corresponding to the action ACT1 is provided at an earlier state than another auxiliary reward [d^2*REa2(−)] corresponding to the action ACT2. In this case, the auxiliary reward REa0(−) is not provided with the discount factor, and the auxiliary reward [d*REa1(+)] is provided with the discount factor "d", and the auxiliary reward [d^2*REa2(−)] is provided with a squared value of the discount factor, i.e., "d^2". In other words, the discount factor d will gradually reduce the reward in later stages.

In some embodiments, a proper boundary of the auxiliary rewards can be determined in the following paragraphs, to ensure that the auxiliary rewards do not affect the original Markov decision process (MDP). The auxiliary rewards can be calculated as:

$$Y \times (\text{a number of positive symptoms in the new state} * \lambda)$$

$$-(\text{a number of positive symptoms in the current state} * \lambda)$$

Y is in a range between K/(K+1) and 1, in which, variable K is equal to a minimum between a number of positive symptom or the budget "t". A is a positive constant value.

In some embodiments, the negative auxiliary reward REa0(−), can be calculated as:

$$Y \times (1*\lambda)-(1*\lambda)$$

Since the Y is in a range between K/(K+1) and 1, the negative auxiliary reward REa0(−), Y×(1*λ)−(1*λ), will be a negative value, which can be regarded as a penalty for selecting a symptom inquiry with a negative answer.

The positive auxiliary reward REa1(+), can be calculated as:

$$Y \times (2*\lambda)-(1*\lambda)$$

Since the Y is in a range between K/(K+1) and 1, the negative auxiliary reward REa1(+), Y×(2*λ)−(1*λ), will be a positive value, which can be regarded as a reward for selecting a symptom inquiry with a positive answer.

The negative auxiliary reward REa2(−), can be calculated as:

$$Y \times (2*\lambda)-(2*\lambda)$$

Since the Y is in a range between K/(K+1) and 1, the negative auxiliary reward REa2(−), Y×(2*λ)−(2*λ), will be a negative value, which can be regarded as a penalty for selecting a symptom inquiry with a negative answer.

In order to encourage the reinforcement learning agent to discover positive symptoms more quickly, a simple heuristic is to provide the agent with an auxiliary piece of reward when a positive symptom is queried, and a relatively smaller (or even negative) reward when a negative symptom is queried. The aforesaid control method 200a shown in FIG. 2A can be called as reward shaping, which changes the original reward function of an MDP into a new one in order to make the reinforcement learning problem easier to solve. Given that certain important negative symptoms are also helpful to distinguish diseases, it is counterintuitive to punish an agent with non-positive auxiliary rewards when it queries negative symptoms. Limiting boundary of the auxiliary rewards in the control method 200a guarantees the invariance of the optimal policy with auxiliary rewards. Therefore, even though the agent may receive non-positive auxiliary rewards, it can still learn to query those critical negative symptoms.

Figure 2B:
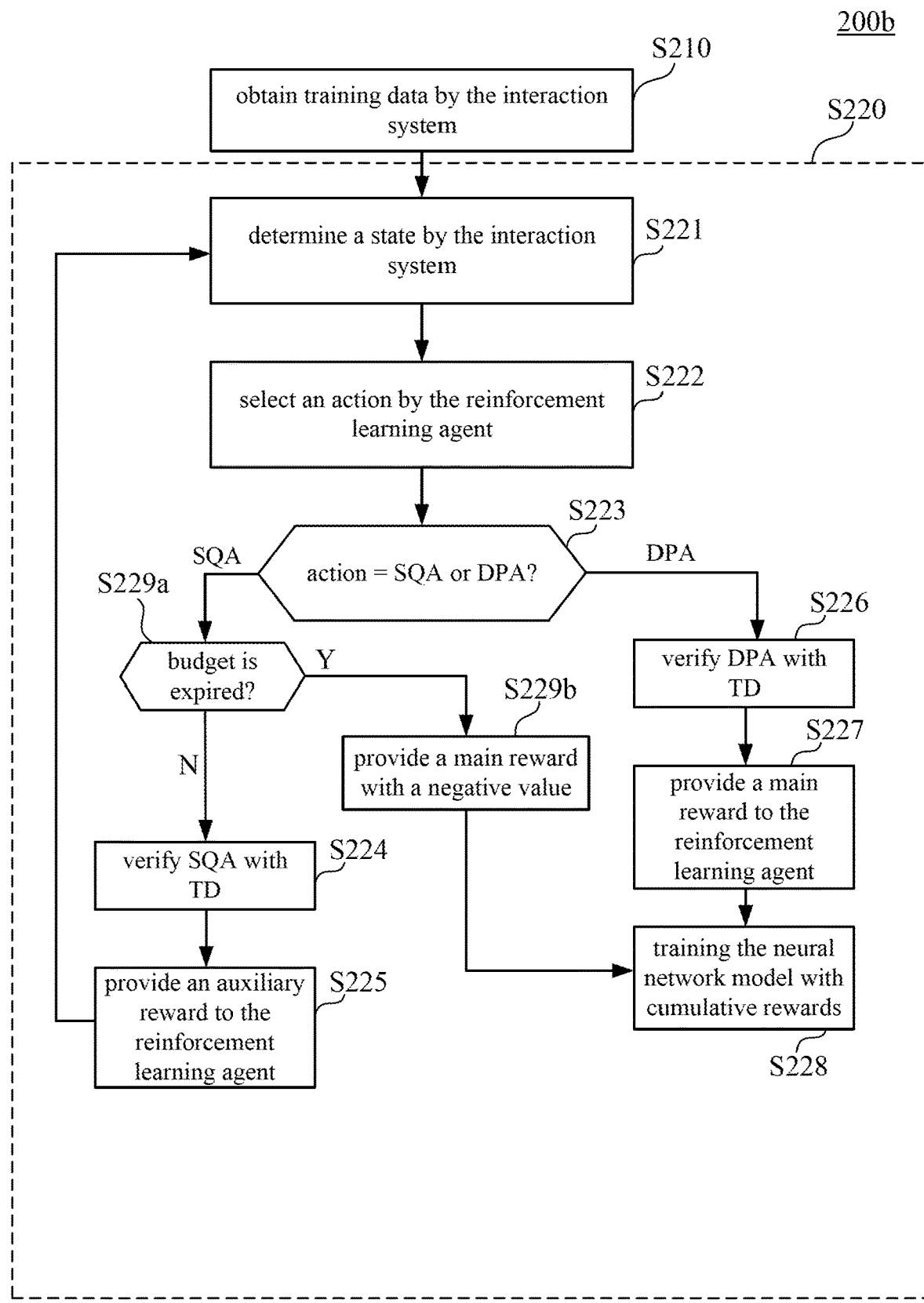
FIG. 2B is another flow chart illustrating a control method about how the neural network model is trained by the medical system in FIG. 1 according to some embodiments of the disclosure.

In aforesaid embodiments shown in FIG. 1 and FIG. 2A, when the budget "t" is expired, the reinforcement learning agent 140 as shown in FIG. 1 and FIG. 2A will select one candidate action from the disease prediction actions DPA, not from the symptom inquiry actions SQA. However, the disclosure is not limited thereto. Reference is further made to FIG. 2B, which is another chart illustrating a control method 200b about how the neural network model is trained by the medical system in FIG. 1 according to some embodiments of the disclosure. Compared to embodiments shown in FIG. 2A, the control method 200b shown in FIG. 2B further include operation S229a and S229b. In embodiments shown in FIG. 2B, the reinforcement learning agent 140 can select one action from the disease prediction actions DPA and the symptom inquiry actions SQA, regardless of the budget "t". In other words, it is possible that the reinforcement learning agent 140 select one of the symptom inquiry actions SQA when the budget "t" is expired. As shown in FIG. 2B, the operation S229a is performed, after the operation S223 and before the operation S224, to determine whether the budget is expired. If the current action is one of the symptom inquiry actions SQA and the budget "t" is not expired, the control method 200b will go to the operation S224.

If the current action is one of the symptom inquiry actions SQA and the budget "t" is expired, the operation S229b will be performed to provide the main reward with a negative value (e.g., the main reward equals to "−1"), and the operation S228 is performed to train the neural network model NNM with the cumulative rewards. In this case, the main reward with the negative value in aforesaid training process will suggest the reinforcement learning agent 140 to avoid selecting one of the symptom inquiry actions SQA when the budget "t" is expired.

Figure 5:
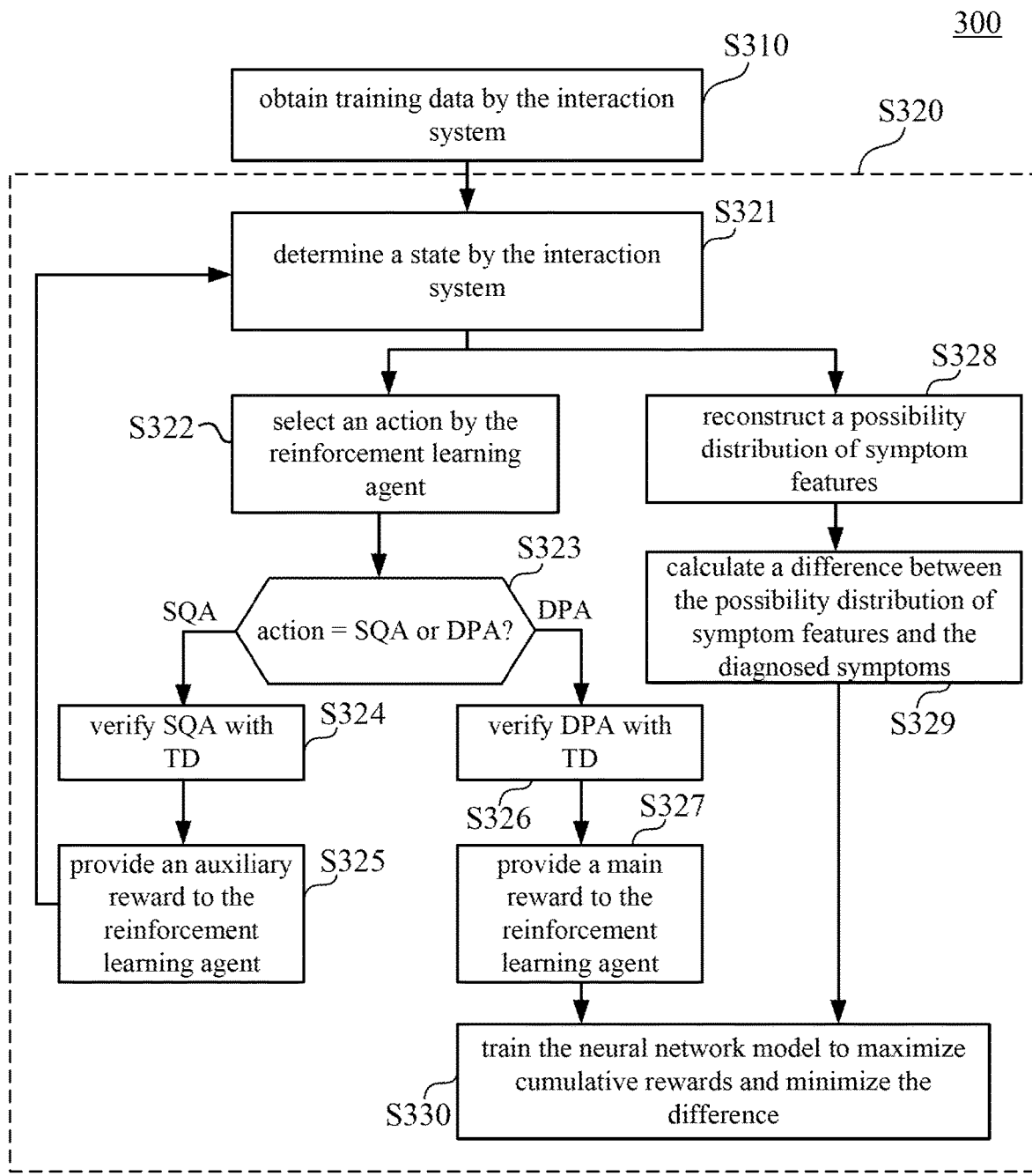
FIG. 5 is a schematic diagram illustrating a control method according to some embodiments of the disclosure.

Reference is further made to FIG. 5, which is a schematic diagram illustrating a control method 300 according to some embodiments of the disclosure. In embodiments shown in FIG. 5, the operation S310 and S321-S327 are similar to the operation S210 and S221-S227 in aforesaid embodiments shown in FIG. 2A, and not to be repeated here.

Figure 6:
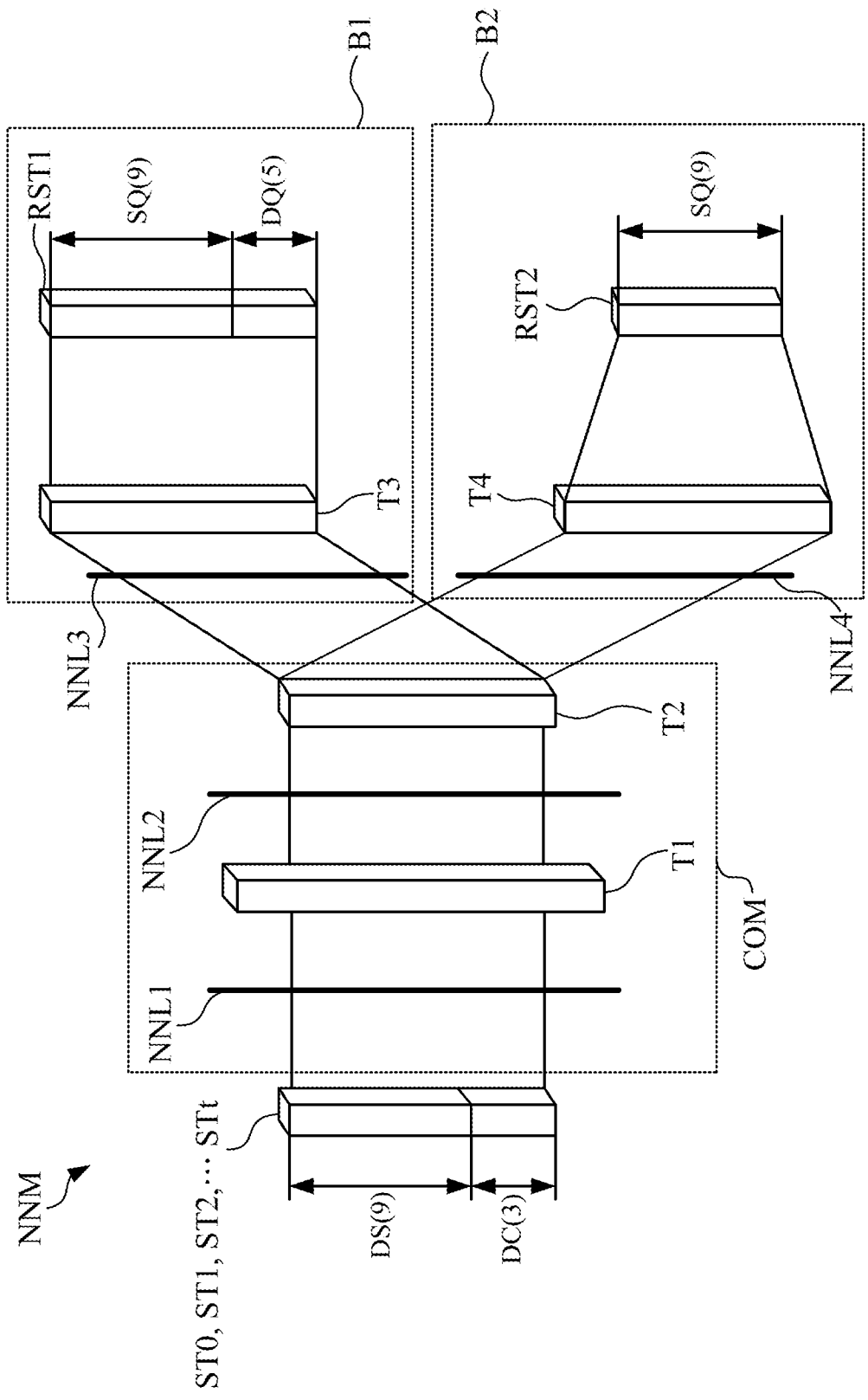
FIG. 6 is a schematic diagram illustrating a structure of the neural network model according to some embodiments of the disclosure.

As shown in FIG. 5, the control method 300 further includes operations S328, S329 and S330. In the embodiments shown in FIG. 5, the neural network model NNM utilized by the reinforcement learning agent 140 in FIG. 1, can be a dual neural network model. Reference is further made to FIG. 6, which is a schematic diagram illustrating a structure of the neural network model NNM according to some embodiments of the disclosure. As shown in FIG. 6, the neural network model NNM, utilized by the reinforcement learning agent 140 for selecting the sequential actions, includes a common neural network portion COM, a first branch neural network portion B1 and a second branch neural network portion B2.

As shown in FIG. 5, the control method 300 further includes operations S328, S329 and S330 in addition to embodiments of the control method 200a shown in FIG. 2A. However, the disclosure is not limited thereto. In a similar way, the operations S328, S329 and S330 of the control method 300 can be applied to embodiments as the control method 200b (which includes operations S229a and S229b) shown in FIG. 2B.

As shown in FIG. 6, the common neural network portion COM includes a neural network layer NNL1 to convert the input state ST0-STt into an intermediate tensor T1, and another neural network layer NNL2 to convert the intermediate tensor T1 into another intermediate tensor T2. In some embodiments, the neural network layer NNL1 and the neural network layer NNL2 can be fully-connection layers or convolution filter layers.

As shown in FIG. 6, the first branch neural network portion B1 and the second branch neural network portion B2 are respectively connected to the common neural network portion COM.

As shown in FIG. 6, the first branch neural network portion B1 includes a neural network layer NNL3 to convert the intermediate tensor T2 into another intermediate tensor T3. In some embodiments, the neural network layer NNL3 can be a fully-connection layer or a convolution filter layer. The intermediate tensor T3 in the first branch neural network portion B1 is processed by a fully-connection layer into a first result state RST1 generated by the first branch neural network portion B1. The first result state RST1 generated by the first branch neural network portion B1 is utilized to select a symptom inquiry action or a result prediction action (including a disease prediction action and/or a medical department recommendation action corresponding to the disease prediction action), such as the operation S221-S227 discussed in aforesaid embodiments in FIG. 2A or FIG. 2B or similar operation S321-S327 in FIG. 5.

As shown in FIG. 6, the second branch neural network portion B2 includes a neural network layer NNL4 to convert the intermediate tensor T2 into another intermediate tensor T4. In some embodiments, the neural network layer NNL4 can be a fully-connection layer or a convolution filter layer. The intermediate tensor T4 in the second branch neural network portion B2 is processed by another fully-connection layer into a second result state RST2 generated by the second branch neural network portion B2. The second result state RST2 generated by the second branch neural network portion B2 is utilized to reconstruct a possibility distribution of symptom features.

Figure 7:
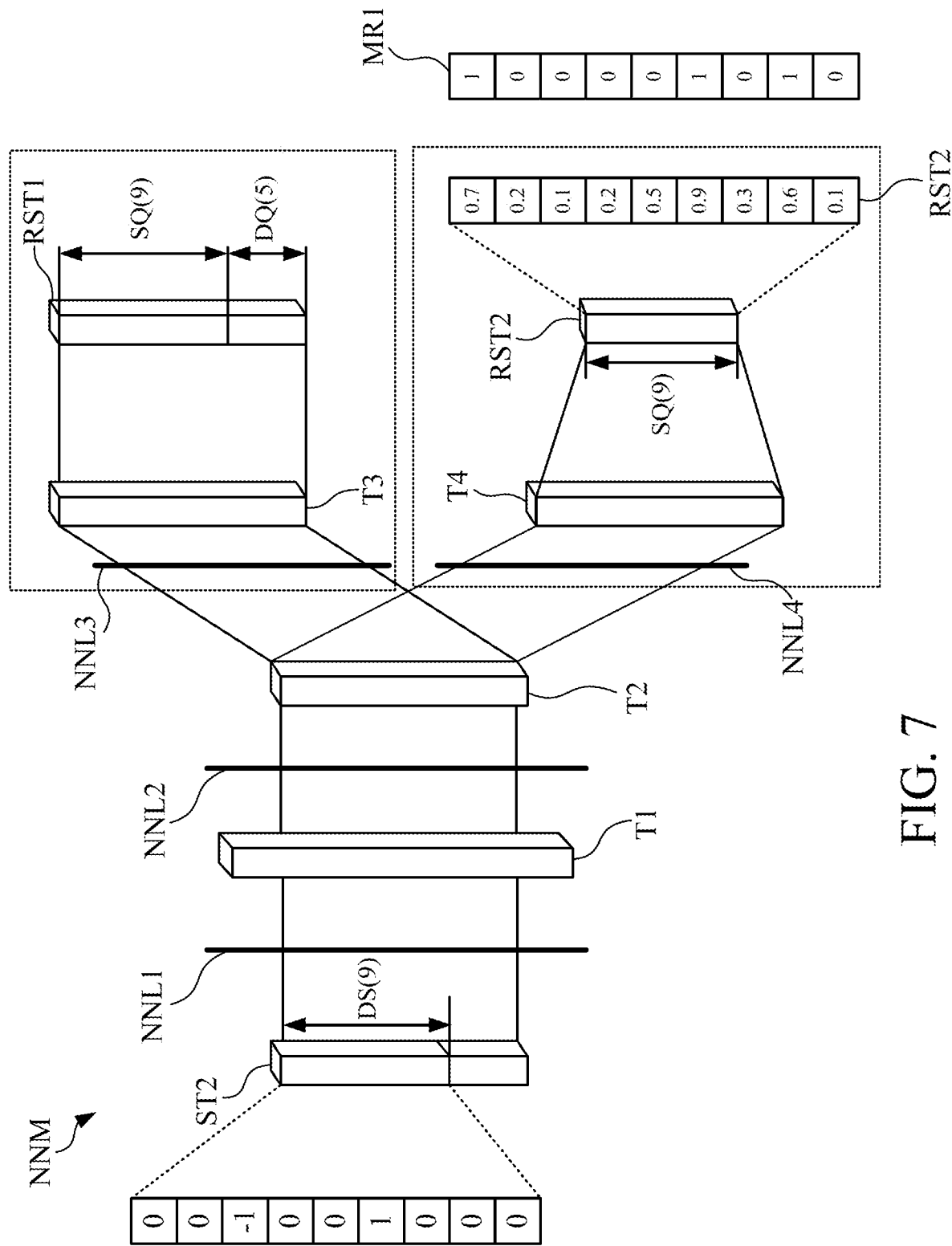
FIG. 7 is a schematic diagram illustrating a demonstration example of the second result state when the input state to the neural network model is the state shown in FIG. 4B and FIG. 4C.

Reference is further made to FIG. 7, which is a schematic diagram illustrating a demonstration example of the second result state RST2 when the input state to the neural network model NNM is the state ST2 shown in FIG. 4B and FIG. 4C. As shown in FIG. 4B, FIG. 4C and FIG. 7, the input state, i.e., the state ST2, has only include information about two symptoms (the third symptom is negative and the sixth symptom is positive). It is hard to tell a whole picture of the symptom distribution of the current state, because most of the symptoms remains unconfirmed (there are seven symptoms are unconfirmed in the embodiment shown in FIG. 7). In the embodiments shown in FIG. 5, FIG. 6 and FIG. 7, operation S328 is performed, based on the second branch neural network portion B2 of the neural network model NNM, to reconstruct a possibility distribution of symptom features according to the input state ST2, while the first branch neural network portion B1 of the neural network model NNM is processing to select the sequential actions (in operation S322-S327).

As shown in FIG. 7, based on the branch neural network portion B2, the second result state RST2 shown a possibility distribution of symptom features. As shown in FIG. 7, the possibility corresponding to the first symptom to the ninth symptom is calculated to be 0.7, 0.2, 0.1, 0.2, 0.5, 0.9, 0.3, 0.6 and 0.1 respectively by the branch neural network portion B2. As shown in FIG. 5, operation S329 is performed, by the interaction system 120 or the reinforcement learning agent 140, to calculate a difference between the possibility distribution of symptom features and the diagnosed symptoms in the medical record MR1 (regarded as the ground truth) of the training data TD. In some embodiments, the difference between the possibility distribution of symptom features and the diagnosed symptoms in the medical record MR1 can be calculated by squared values of deduction values between the possibility distribution of symptom features and the diagnosed symptoms in the medical record MR1. For example, regarding to the first symptom features and the first diagnosed symptom as shown in FIG. 7, the difference can be calculated as $(0.7-1)^2$. The total difference between the possibility distribution of symptom features and the diagnosed symptoms in the medical record MR1 can be calculated as:

$$(0.7-1)^2+(0.2-0)^2+(0.1-0)^2+\ldots+(0.1-0)^2$$

When the total difference is larger, it means that the current neural network model NNM is not effective in reconstructing the possibility distribution of symptom features. In this case, the current neural network model NNM will be updated in following training process.

In some embodiments, the difference between the possibility distribution of symptom features and the diagnosed symptoms in the medical record MR1 can be calculated by Binary Cross Entropy (BCE) loss function, but the difference between the possibility distribution of symptom features and the diagnosed symptoms in the medical record MR1 is not limited to be calculated in aforesaid manner.

As shown in FIG. 5, operation S330 is performed to train the neural network model NNM in FIG. 1 to maximize the cumulative rewards (including the auxiliary rewards and the main reward collected in operations S322-S327) to the reinforcement learning agent 140 and also to minimize a difference between the possibility distribution of symptom features and the diagnosed symptoms.

In other words, an objective function of the neural network model NNM during training can be configured as:

the cumulative rewards−β*(the cumulative value of BCE loss)

In aforesaid objective function, β is a hyper-parameter, which can control the importance of the reconstruction task. The neural network model NNM is trained to maximize this objective function, which means to maximize the cumulative rewards and to minimize the difference between the possibility distribution of symptom features and the diagnosed symptoms. In the embodiments shown in FIG. 5, the auxiliary rewards are provided in operations S325 and the reconstruction of the symptom features are executed in operations S328-S329. However, the disclosure is not limited to perform all of these operations.

Figure 8:
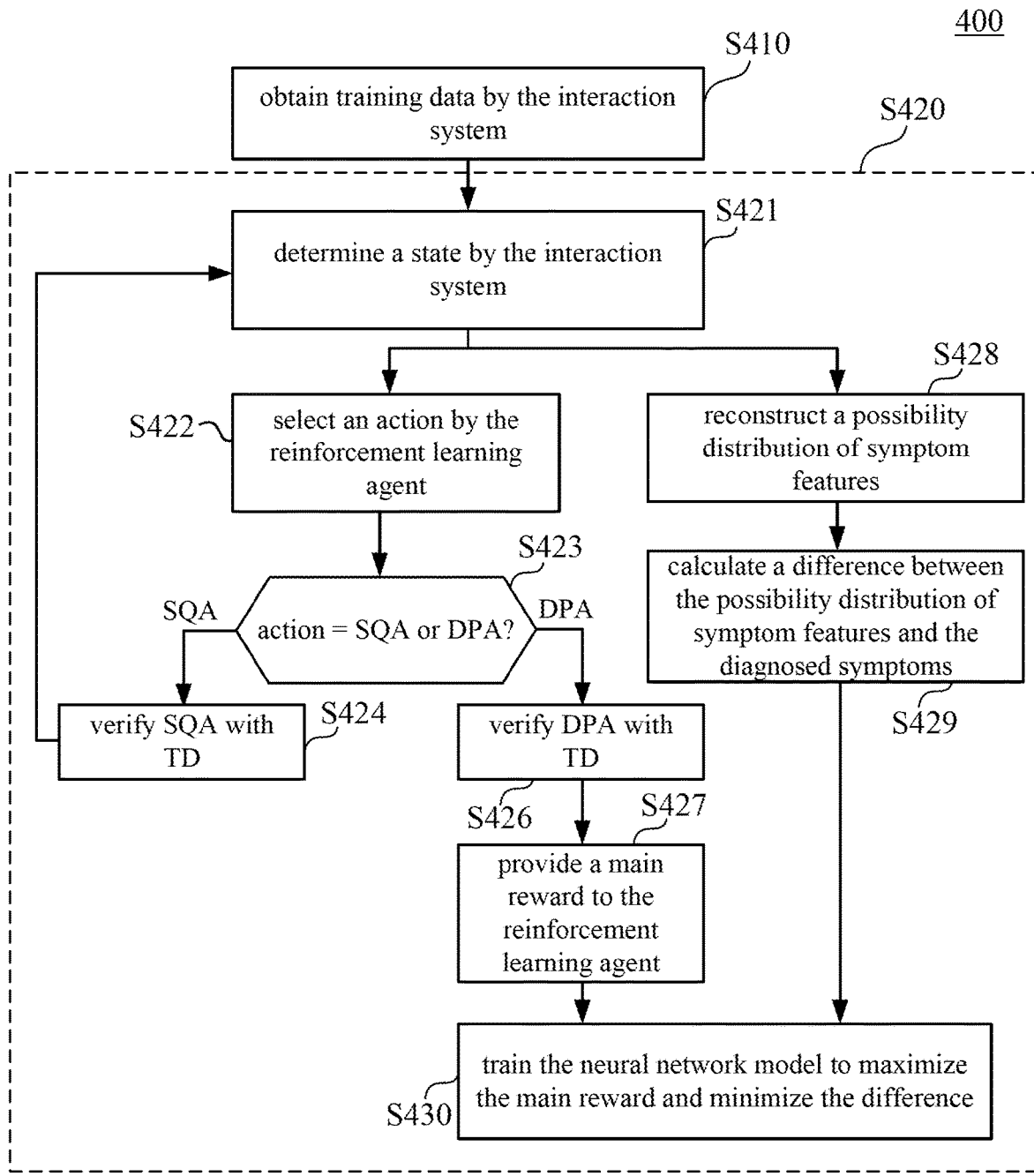
FIG. 8 is a flow chart illustrating a control method according to some embodiments of the disclosure.

Reference is further made to FIG. 8, which is a flow chart illustrating a control method 400 according to some embodiments of the disclosure. Operations S410, S421, S422, S423, S424, S426 and S427 are similar to the operations S210, S221, S222, S223, S224, S226 and S227 in embodiments shown in FIG. 2A, and operations S428 and S429 are similar to the operations S328 and S329 in embodiment shown in FIG. 5. It is noticed that the control method 400 does not provide any auxiliary rewards. In this embodiments, the operation S430 is performed to train the neural network model NNM in FIG. 1 to maximize the main reward (in operation S427) and also to minimize a difference between the possibility distribution of symptom features and the diagnosed symptoms (in operation S429). In this case, the objective function of the neural network model NNM during training can be configured as:

the cumulative rewards−β*(the cumulative value of BCE loss)=the main reward−β*(the cumulative value of BCE loss)

Figure 9:
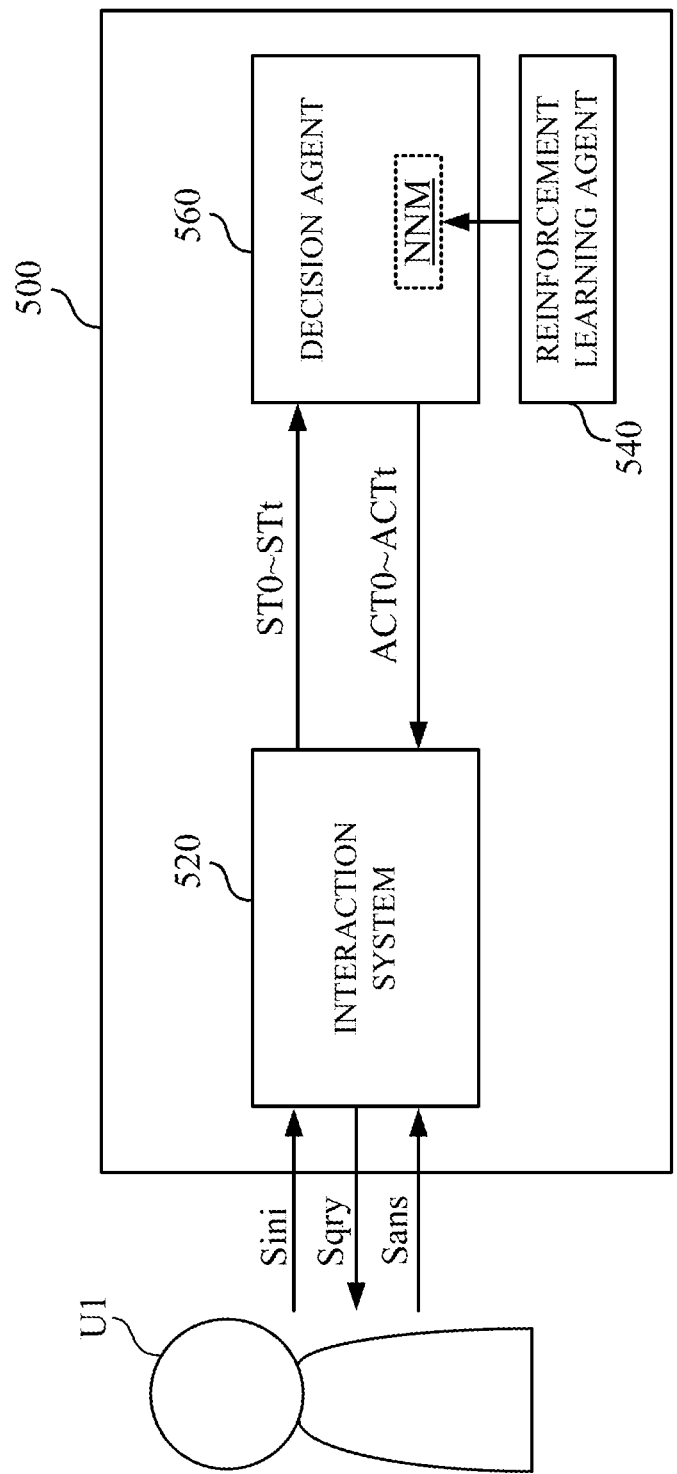
FIG. 9 is a schematic diagram illustrating the medical system after the training of the neural network model is done.

After the neural network model NNM is trained according the control method 200a, 200b, 300 or 400 in FIG. 2A, FIG. 2B, FIG. 5 or FIG. 8, the medical system 100 in FIG. 1 is able to be utilized to interact with a patient and provide a disease prediction to the patient according to an initial symptom and patient's answers to the symptom inquiries. Reference is further made to FIG. 9, which is a schematic diagram illustrating the medical system 500 after the training of the neural network model NNM is done. In this case, the interaction system 520 may include an input/output interface, such as keyboard, mouse, microphone, touch panel or any equivalent device, to interact with a user U1. As shown in FIG. 9, the medical system 500 further include a decision agent 560, which utilize the neural network model NNM trained by the reinforcement learning agent 540.

The medical system 500 is configured to interact with the user U1 through the input/output interface (e.g. collecting an initial symptom from the user U1, providing some symptom inquiries to the user U1 and/or collecting corresponding symptom responses from the user U1). Based on aforesaid interaction history, the medical system 500 is able to analyze, diagnose or predict a potential disease occurring to the user U1.

In some embodiments, the medical system 500 is established with a computer, a server or a processing center. The interaction system 520, the reinforcement learning agent 540 and the decision agent 560 can be implemented by a processor, a central processing unit or a computation unit. In some embodiments, the interaction system 520 can further include an output interface (e.g., a display panel for display information) and an input device (e.g., a touch panel, a keyboard, a microphone, a scanner or a flash memory reader) for user to type text commands, to give voice commands or to upload some related data (e.g., images, medical records, or personal examination reports).

In some other embodiments, at least a part of the medical system 500 is established with a distribution system. For example, the interaction system 520, the reinforcement learning agent 540 and the decision agent 560 can be established by a cloud computing system.

As shown in FIG. 9, the input/output interface of the interaction system 520 can be manipulated by a user U1. The user U1 can see the information displayed on the input/output interface and the user U1 can enter his/her inputs on the input/output interface. In an embodiment, the input/output interface will display a notification to ask the user U1 about his/her symptoms. The first symptom inputted by the user U1 will be regarded as an initial symptom Sini. The input/output interface is configured for collecting the initial symptom Sini according to the user's manipulation as the state ST0. The interaction system 520 transmits the state ST0 to the decision agent 560.

The decision agent 560 is configured for selecting sequential actions ACT0-ACTt. The sequential actions ACT0-ACTt include symptom inquiry actions and a result prediction action. The result prediction action can be a disease predication action and/or a medical department recommendation action corresponding to the disease prediction action. The interaction system 520 will generate symptom inquiries Sqry according to the sequential actions ACT0-ACTt. The symptom inquiries Sqry are displayed sequentially, and the user U1 can answer the symptom inquiries Sqry. The interaction system 520 is configured for receiving symptom responses Sans corresponding to the symptom inquiries Sqry and converting the symptom responses Sans into the states ST1-STt. After a few inquiries (when the budget is expired), the medical system 500 shown in FIG. 9 will provide a disease prediction or a medical department recommendation to the user according to the result prediction action.

The decision agent 560 will decide optimal questions (i.e., the symptom inquiries Sqry) to ask the user U1 according to the initial symptom Sini and all previous responses Sans (before the current question) based on the trained neural network model NNM.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A control method, suitable for a reinforcement learning system, the control method comprising:
    obtaining training data related to an interaction system, the interaction system interacting with a reinforcement learning agent, the reinforcement learning agent being configured for selecting sequential actions, the training data comprising a medical record indicating a relationship between a diagnosed disease and diagnosed symptoms related to the diagnosed disease;
    training a neural network model to maximize cumulative rewards collected by the reinforcement learning agent in response to the sequential actions, wherein the neural network model is utilized by the reinforcement learning agent for selecting the sequential actions from a set of candidate actions, the sequential actions comprises a plurality of symptom inquiry actions and a result prediction action; and
    during training of the neural network model, providing auxiliary rewards of the cumulative rewards to the reinforcement learning agent according to a comparison between the symptom inquiry actions and the diagnosed symptoms, and providing a main reward of the cumulative rewards to the reinforcement learning agent according to a comparison between the result prediction action and the diagnosed disease,
    wherein the neural network model comprises a common neural network portion, a first branch neural network portion and a second branch neural network portion, the first branch neural network portion and the second branch neural network portion are respectively connected to the common neural network portion, a first result state generated by the first branch neural network portion is utilized to select the symptom inquiry actions or the result prediction action, a second result state generated by the second branch neural network portion is utilized to reconstruct a possibility distribution of symptom features.

2. The control method as claimed in claim 1, wherein the operation of providing the auxiliary rewards comprises:
    comparing each one of the symptom inquiry actions with the diagnosed symptoms in the training data; and
    in response to one of the symptom inquiry actions matching one of the diagnosed symptoms in the training data, providing a positive auxiliary reward; and
    in response to the one of the symptom inquiry actions failing to match any one of the diagnosed symptoms in the training data, providing a negative auxiliary reward.

3. The control method as claimed in claim 2, wherein the operation of providing the auxiliary rewards comprises:
    determining whether a currently-selected one of the symptom inquiry actions and a previously-selected one of the symptom inquiry actions direct to one same symptom; and
    in response to the currently-selected one of the symptom inquiry actions and the previously-selected one of the symptom inquiry actions directing to the same symptom, providing the negative auxiliary reward.

4. The control method as claimed in claim 2, wherein the auxiliary rewards in a sequential order are provided with gradually increasing discounts.

5. The control method as claimed in claim 4, wherein a first auxiliary reward of the auxiliary rewards is provided at an earlier state than a second auxiliary reward of the auxiliary rewards, and the second auxiliary reward is provided with a discount factor.

6. The control method as claimed in claim 1, wherein an objective function of the neural network model during training comprises to maximize the cumulative rewards and to minimize a difference between the possibility distribution of symptom features and the diagnosed symptoms.

7. The control method as claimed in claim 1, wherein the sequential actions selected by the reinforcement learning agent cause the interaction system to move from one state to another state, state data of the interaction system comprises symptom data bits and context data bits, the symptom data bits indicate a positive status, a negative status or an unconfirmed status of symptoms occurred to a patient in the medical record, the context data bits indicate related information of the patient in the medical record.

8. The control method as claimed in claim 1, wherein the result prediction action comprises at least one of a disease prediction action and a medical department recommendation action corresponding to the disease prediction action.

9. The control method as claimed in claim 1, wherein after the neural network model is trained, the control method further comprising:
    collecting an initial symptom by the interaction system from a user as an initial state to the reinforcement learning agent;
    selecting the sequential actions according to the neural network model; and
    providing a disease prediction or a medical department recommendation to the user according to the result prediction action of the sequential actions.

10. A system, comprising:
    an interaction system;
    a reinforcement learning agent interacting with the interaction system, the reinforcement learning agent is configured to select sequential actions; and
    a neural network model, trained by the reinforcement learning agent in reference to interactions between the interaction system and the reinforcement learning agent according to training data, the training data comprising a medical record indicating a relationship between a diagnosed disease and diagnosed symptoms related to the diagnosed disease,
    wherein the neural network model is utilized by the reinforcement learning agent for selecting the sequential actions from a set of candidate actions, the neural network model is trained to maximize cumulative rewards collected by the reinforcement learning agent in response to the sequential actions, the sequential actions comprises a plurality of symptom inquiry actions and a result prediction action, during training of the neural network model, the interaction system provides auxiliary rewards of the cumulative rewards to the reinforcement learning agent according to a comparison between the symptom inquiry actions and the diagnosed symptoms, and the interaction system provides a main reward of the cumulative rewards to the reinforcement learning agent according to a comparison between the result prediction action and the diagnosed disease, wherein the neural network model comprises a common neural network portion, a first branch neural network portion and a second branch neural network portion, the first branch neural network portion and the second branch neural network portion are respectively connected to the common neural network portion, a first result state generated by the first branch neural network portion is utilized to select a symptom inquiry action or a result prediction action, a second result state generated by the second branch neural network portion is utilized to reconstruct a possibility distribution of symptom features.

11. The system as claimed in claim 10, wherein during providing the auxiliary rewards, the interaction system compares each one of the symptom inquiry actions with the diagnosed symptoms in the training data, the interaction system provides a positive auxiliary reward in response to one of the symptom inquiry actions matching one of the diagnosed symptoms in the training data, and the interaction system provides a negative auxiliary reward in response to the one of the symptom inquiry actions failing to match any one of the diagnosed symptoms in the training data.

12. The system as claimed in claim 11, wherein the interaction system determines whether a currently-selected one of the symptom inquiry actions and a previously-selected one of the symptom inquiry actions direct to one same symptom, and in response to the currently-selected one of the symptom inquiry actions and the previously-selected one of the symptom inquiry actions directing to the same symptom, the interaction system provides the negative auxiliary reward.

13. The system as claimed in claim 11, wherein the auxiliary rewards in a sequential order are provided with gradually increasing discounts.

14. The system as claimed in claim 13, wherein a first auxiliary reward of the auxiliary rewards is provided by the interaction system at an earlier state than a second auxiliary reward of the auxiliary rewards, and the second auxiliary reward is provided with a discount factor.

15. The system as claimed in claim 10, wherein an objective function of the neural network model during training comprises to maximize the cumulative rewards and to minimize a difference between the possibility distribution of symptom features and the diagnosed symptoms.

16. The system as claimed in claim 10, wherein the sequential actions selected by the reinforcement learning agent causes the interaction system to move from one state to another next state, state data of the interaction system comprises symptom data bits and context data bits, the symptom data bits indicate a positive status, a negative status or an unconfirmed status of symptoms occurred to a patient in the medical record, the context data bits indicate related information of the patient in the medical record.

17. The system as claimed in claim 10, wherein the result prediction action comprises at least one of a disease prediction action and a medical department recommendation action corresponding to the disease prediction action.

18. The system as claimed in claim 10, wherein the system comprises a decision agent, after the neural network model is trained, the interaction system collects an initial symptom from a user as an initial state to the decision agent, the decision agent selects the sequential actions according to the neural network model, and the interaction system provides a disease prediction to the user according to the result prediction action.

\* \* \* \* \*